US00PP18992P2

(12) United States Plant Patent
Jepsen

(10) Patent No.: US PP18,992 P2
(45) Date of Patent: Jul. 1, 2008

(54) *KALANCHOE* PLANT NAMED 'KELLY'

(50) Latin Name: *Kalanchoe blossfeldiana*
Varietal Denomination: Kelly

(75) Inventor: Knud Jepsen, Hinnerup (DK)

(73) Assignee: Knup Jepsen A/S, Hinnerup (DK)

( * ) Notice: Subject to any disclaimer, the term of this patent is extended or adjusted under 35 U.S.C. 154(b) by 0 days.

(21) Appl. No.: 11/633,108

(22) Filed: Dec. 1, 2006

(51) Int. Cl.
*A01H 5/00* (2006.01)

(52) U.S. Cl. ..... Plt./335

(58) Field of Classification Search ..... Plt./335
See application file for complete search history.

*Primary Examiner*—Anne Marie Grunberg
*Assistant Examiner*—Louanne Krawczewicz Myers
(74) *Attorney, Agent, or Firm*—C. A. Whealy

(57) ABSTRACT

A new and distinct cultivar of *Kalanchoe* plant named 'Kelly', characterized by its upright, uniform and moderately vigorous growth habit; dark green-colored leaves; uniform, freely and early flowering habit; large double dark orange and light orange bi-colored flowers; and excellent postproduction longevity.

1 Drawing Sheet

Botanical designation: *Kalanchoe blossfeldiana.*
Cultivar denomination: 'Kelly'.

BACKGROUND OF THE INVENTION

The present invention relates to a new and distinct cultivar of *Kalanchoe,* botanically known as *Kalanchoe blossfeldiana,* and hereinafter referred to by the name 'Kelly'.

The new *Kalanchoe* is a product of a planned breeding program conducted by the Inventor in Hinnerup, Denmark. The objective of the breeding program is to create new double-flowered *Kalanchoe* cultivars with attractive foliage and flower coloration.

The new *Kalanchoe* originated from a self-pollination made by the Inventor in Hinnerup, Denmark in September 2003, of a proprietary *Kalanchoe blossfeldiana* selection identified as code number KJ 2003 0564, not patented. The cultivar Kelly was discovered and selected by the Inventor as a flowering plant from within the progeny of the stated self-pollination in a controlled environment in Hinnerup, Denmark in May, 2004.

Asexual reproduction of the new *Kalanchoe* by vegetative terminal cuttings in a controlled environment in Hinnerup, Denmark since July, 2004, has shown that the unique features of this new *Kalanchoe* are stable and reproduced true to type in successive generations.

SUMMARY OF THE INVENTION

The cultivar Kelly has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Kelly'. These characteristics in combination distinguish 'Kelly' as a new and distinct cultivar of *Kalanchoe:*

1. Upright, uniform and moderately vigorous growth habit.

2. Dark green-colored leaves.
3. Uniform, freely and early flowering habit.
4. Large double dark orange and light orange bi-colored flowers.
5. Excellent postproduction longevity.

Plants of the new *Kalanchoe* can be compared to plants of the parent selection. Plants of the new *Kalanchoe* differ from plants of the parent selection in the following characteristics:

1. Plants of the new *Kalanchoe* are more compact than plants of the parent selection.
2. Plants of the new *Kalanchoe* have slightly smaller flowers than plants of the parent selection.
3. Plants of the new *Kalanchoe* have double flowers whereas plants of the parent selection have single flowers.

Plants of the new *Kalanchoe* can be compared to plants of the *Kalanchoe blossfeldiana* cultivar Sarah, disclosed in a U.S. Plant patent application Ser. No. 11/633,112, filed concurrently. In side-by-side comparisons conducted in Hinnerup, Denmark, plants of the new *Kalanchoe* differed from plants of the cultivar Sarah in the following characteristics:

1. Plants of the new *Kalanchoe* were more compact and had shorter internodes than plants of the cultivar Sarah.
2. Flowers of plants of the new *Kalanchoe* had larger flowers than plants of the cultivar Sarah.
3. Plants of the new *Kalanchoe* had double flowers whereas plants of the cultivar Sarah had single flowers.
4. Plants of the new *Kalanchoe* and the cultivar Sarah differed in flower color.
5. Plants of the new *Kalanchoe* flowered about four days later than plants of the cultivar Sarah.

BRIEF DESCRIPTION OF THE PHOTOGRAPHS

The accompanying colored photographs illustrate the overall appearance of the new *Kalanchoe,* showing the colors as true as it is reasonably possible to obtain in colored reproductions of this type. Colors in the photographs may differ slightly from the color values cited in the detailed botanical description which accurately describe the colors of the new *Kalanchoe*.

The photograph at the top of the sheet comprises a side perspective view of a typical flowering plant of 'Kelly' grown in a container.

The photograph at the bottom of the sheet comprises a top perspective view of a typical flowering plant of 'Kelly' grown in a container.

DETAILED BOTANICAL DESCRIPTION

The aforementioned photographs and following observations, measurements and values describe plants grown in Hinnerup, Denmark in a glass-covered greenhouse during the summer and under conditions which closely approximate commercial production. During the production of the plants, day temperatures were about 19° C., night temperatures were about 21° C. and light levels ranged from 10 kilolux to 50 kilolux. Unrooted cuttings were directly stuck in 10-cm containers and received long day/short night conditions (more than 14 hours of light) for about two weeks; plants then received photoinductive short day/long night conditions (minimum 14 hours darkness) until flowering. Plants were about 12 weeks old when the photographs and the description were taken. In the detailed description, color references are made to The Royal Horticultural Society Color Chart, 2001 Edition, except where general terms of ordinary dictionary significance are used.

Botanical classification: *Kalanchoe blossfeldiana* cultivar Kelly.

Parentage:

*Female, or seed, parent.*—Proprietary selection of *Kalanchoe blossfeldiana* identified as code number KJ 2003 0564, not patented.

*Male or pollen parent.*—Proprietary selection of *Kalanchoe blossfeldiana* identified as code number KJ 2003 0564, not patented.

Propagation:

*Type.*—By vegetative terminal cuttings.

*Time to initiate roots, summer.*—About two weeks at temperatures of 19° C. to 21° C.

*Time to initiate roots, winter.*—About three weeks at temperatures of 19° C. to 21° C.

*Time to produce a rooted young plant, summer.*—About 21 days at temperatures of 19° C. to 21° C.

*Time to produce a rooted young plant, winter.*—About 24 days at temperatures of 19° C. to 21° C.

*Root description.*—Fine, fibrous; white in color.

*Rooting habit.*—Freely branching; moderately dense.

Plant description:

*Plant habit.*—Upright, uniform and moderately vigorous growth habit. Very freely flowering with numerous compound cymes. Inverted triangle with rounded crown. Appropriate for 6-cm to 10-cm containers.

*Plant height at flowering.*—About 16 cm to 20 cm.

*Plant diameter at flowering.*—About 24 cm.

*Branching habit.*—Usually about four to nine lateral branches develop per plant. Pinching (removal of the terminal apex) is not required but will enhance lateral branch development.

Lateral branch description:

*Length.*—About 13 cm.

*Diameter.*—About 4 mm.

*Internode length.*—About 1 cm to 2 cm.

*Aspect.*—Erect.

*Strength.*—Strong.

*Texture.*—Smooth, glabrous.

*Color.*—146A.

Foliage description:

*Arrangement.*—Opposite, simple; generally symmetrical.

*Quantity of leaves per lateral branch.*—About 4.

*Length, vegetative plants.*—About 8 cm to 12 cm.

*Width, vegetative plants.*—About 5 cm to 7 cm.

*Length, generative plants.*—About 5 cm to 6 cm.

*Width, generative plants.*—About 1 cm to 4 cm.

*Shape.*—Ovate.

*Apex.*—Rounded.

*Base.*—Cuneate.

*Margin.*—Crenate.

*Texture, upper and lower surfaces.*—Glabrous, leathery; succulent.

*Venation pattern.*—Pinnate.

*Color.*—Developing and fully developed foliage, upper surface: 147A; venation, 147A. Developing and fully developed foliage, lower surface: 147B; venation, 147B.

*Petiole.*—Length: About 1 cm to 1.5 cm. Diameter: About 5 mm to 7 mm. Texture, upper and lower surfaces: Smooth, glabrous. Color, upper surface: 147A. Color, lower surface: 147B.

Flower description:

*Flower arrangement and habit.*—Double flowers arranged singly in compound dichasial cymes that arise from leaf axils. Uniform and freely flowering habit with usually about 40 to 60 flowers per inflorescence. Flowers not persistent. Flowers not fragrant.

*Natural flowering season.*—Plants of the new *Kalanchoe* initiate and develop flowers under short day/long night conditions or during the late autumn/winter/early spring. Flower initiation and development can also be induced under artificial short day/long night conditions (at least 14 hours of darkness).

*Time to flower.*—Early flowering habit; under short day/long night photoinductive conditions, about 76 days are required. Actual time to flower is primarily dependent upon temperature and light intensity.

*Post-production longevity.*—Excellent post-production longevity; plants maintain good foliage and flower substance for about six weeks under interior environmental conditions.

*Inflorescence height.*—About 10 cm to 12 cm.

*Inflorescence diameter.*—About 6 cm to 7 cm.

*Flower diameter.*—About 2 cm.

*Flower length (height).*—About 1 cm.

*Flower bud.*—Shape: Ellipsoidal. Length: About 1.5 cm. Diameter: About 3 mm. Color: 29A to 30A.

*Petals.*—Arrangement: About eight fused at the base. Length (largest petals): About 8 mm. Width (largest petals): About 6 mm. Aspect: Slightly upright to eventually recurved. Shape: Ovate. Apex: Mucronate. Margin: Entire. Texture, upper and lower surfaces: Smooth, glabrous. Color: When opening and fully opened, upper surface: Towards the apex, N25A; towards the base, 33A. When opening and fully opened, lower surface: Towards the apex, 29A; towards the base, 30A.

*Sepals.*—Appearance: Four fused at the base. Length: About 8 mm. Width: About 2 mm. Shape: Lanceolate. Apex: Acute. Margin: Entire. Texture, upper and lower surfaces: Smooth, glabrous. Color, immature and mature, upper surface: 144A. Color, immature and mature, lower surface: 144B.

*Peduncles.*—Length: About 2 mm to 10 mm. Diameter: About 1 mm. Aspect: Erect to perpendicular. Strength: Strong. Texture: Smooth, glabrous. Color: 147A.

*Reproductive organs.*—Androecium: Stamen number: About five to ten per flower. Anther shape: Elliptic, flat. Anther size: About 1 mm by 1 mm. Anther color: Close to 22A. Amount of pollen: Scarce. Pollen color: Close to 20A. Gynoecium: Pistil number: About four per flower. Pistil length: About 3 mm. Style length: About 2 mm. Style color: 145A. Stigma shape: Rounded. Stigma color: 145A. Ovary color: Close to 138A.

*Seed.*—Quantity of seeds per ovary: 50–60. Length: About 1 mm. Diameter: About 0.5 mm. Color: 145C.

Temperature tolerance: Plants of the new *Kalanchoe* have been observed to tolerate temperatures from about 5° C. to about 30° C.

Pathogen/pest resistance: Plants of the new *Kalanchoe* have not been observed to be resistant to pests and pathogens common to *Kalanchoes*.

It is claimed:

1. A new and distinct *Kalanchoe* plant named 'Kelly' as illustrated and described.

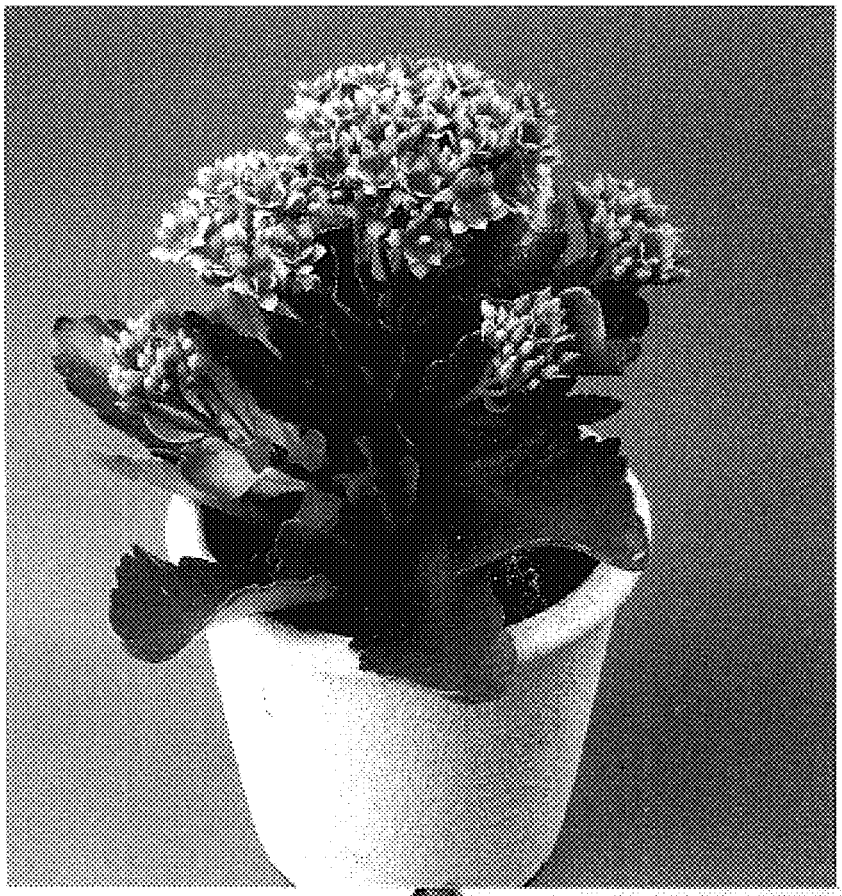
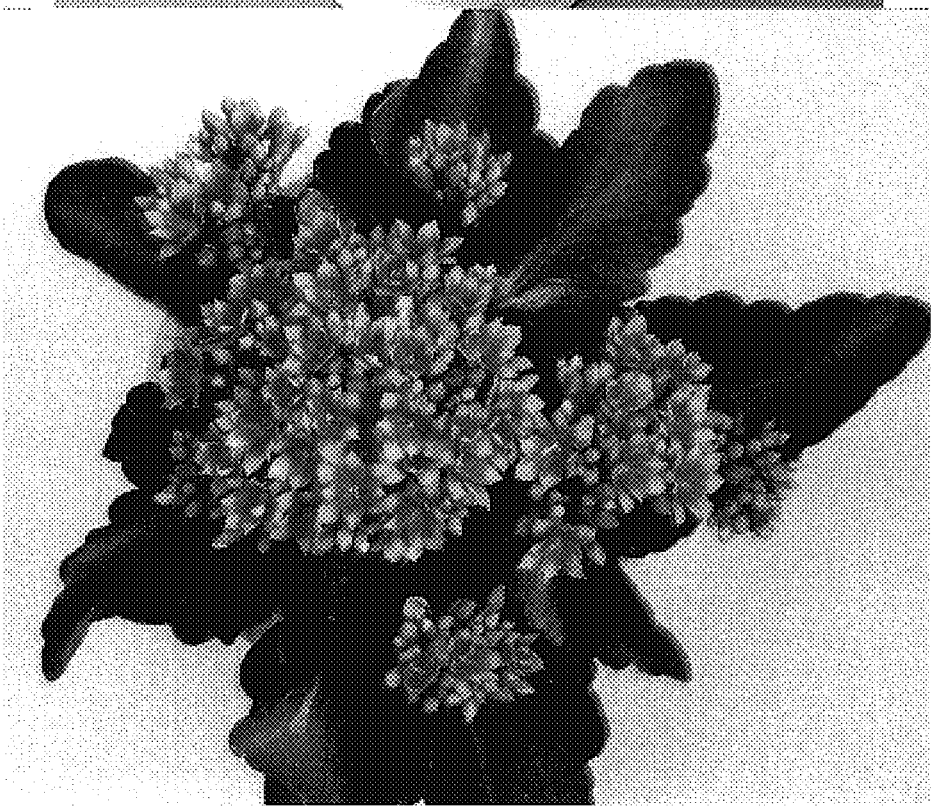

* * * * *